US00PP29021P3

(12) United States Plant Patent
Hofmann

(10) Patent No.: US PP29,021 P3
(45) Date of Patent: Feb. 27, 2018

(54) ***OSTEOSPERMUM* PLANT NAMED 'INOSTYELOW'**

(50) Latin Name: *Osteospermum hybrida*
Varietal Denomination: Inostyelow

(71) Applicant: Silvia Hofmann, Mainz (DE)

(72) Inventor: Silvia Hofmann, Mainz (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 21 days.

(21) Appl. No.: 14/999,745

(22) Filed: Jun. 22, 2016

(65) Prior Publication Data

US 2017/0071114 P1 Mar. 9, 2017

Related U.S. Application Data

(60) Provisional application No. 62/283,675, filed on Sep. 5, 2015.

(51) Int. Cl.
*A01H 5/02* (2006.01)

(52) U.S. Cl.
USPC ..... Plt./360

(58) Field of Classification Search
USPC ..... Plt./360
See application file for complete search history.

(56) References Cited

PUBLICATIONS

UPOV hit on *Osteospermum* named 'Inostyelow', QZ PBR 45340, filed Sep. 8, 2015.*
UPOV hit on *Osteospermum* named 'Inostyelow', CA PBR 16-8935, filed May 26, 2016.*

* cited by examiner

*Primary Examiner* — Anne M Grunberg
(74) *Attorney, Agent, or Firm* — C. A. Whealy

(57) ABSTRACT

A new and distinct cultivar of *Osteospermum* plant named 'Inostyelow', characterized by its compact and upright plant habit; moderately vigorous growth habit; freely branching habit; dense and bushy appearance; early and freely flowering habit; long flowering period; and large inflorescences with golden yellow-colored ray florets and yellow-colored disc florets.

1 Drawing Sheet

Botanical designation: *Osteospermum hybrida.*
Cultivar denomination: 'INOSTYELOW'.

BACKGROUND OF THE INVENTION

The present invention relates to a new and distinct cultivar of *Osteospermum* plant, botanically known as *Osteospermum hybrida* and hereinafter referred to by the name 'Inostyelow'.

The new *Osteospermum* plant is a product of a planned breeding program conducted by the Inventor in Heidesheim, Germany. The objective of the breeding program is to create compact and bushy *Osteospermum* plants with early flowering habit and numerous large attractive flowers.

The new *Osteospermum* plant originated from a cross-pollination made by the Inventor in August, 2008 of *Osteospermum hybrida* 'Balvoyelo', disclosed in U.S. Plant Pat. No. 21,122, as the female, or seed, parent with a proprietary selection of *Osteospermum hybrida* identified as code number O 09 17-1, not patented, as the male, or pollen, parent. The new *Osteospermum* plant was discovered and selected by the Inventor as a single flowering plant from within the progeny of the stated cross-pollination grown in a controlled greenhouse environment in Heidesheim, Germany in March, 2009.

Asexual reproduction of the *Osteospermum* plant by vegetative cuttings in Gensingen, Germany since April, 2009 has shown that the unique features of this new *Osteospermum* plant are stable and reproduced true to type in successive generations.

SUMMARY OF THE INVENTION

Plants of the new *Osteospermum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inostyelow'. These characteristics in combination distinguish 'Inostyelow' as a new and distinct *Osteospermum* plant:

1. Compact and upright plant habit.
2. Moderately vigorous growth habit.
3. Freely branching habit; dense and bushy appearance.
4. Early and freely flowering habit.
5. Long flowering period.
6. Large inflorescences with golden yellow-colored ray florets and yellow-colored disc florets.

Plants of the new *Osteospermum* differ primarily from plants of the female parent, 'Balvoyelo' in plant habit as plants of 'Balvoyelo' are taller and not as dense and bushy.

Plants of the new *Osteospermum* differ primarily from plants of the male parent selection in flowering habit as plants of the new *Osteospermum* flower for a longer period of time than plants of the male parent selection.

Plants of the new *Osteospermum* can be compared to plants of *Osteospermum ecklonis* 'Seikilrem', disclosed in U.S. Plant Pat. No. 13,407. In side-by-side comparisons, plants of the new *Osteospermum* differ from plants of 'Seikilrem' in the following characteristics:

1. Plants of the new *Osteospermum* are upright than plants of 'Seikilrem'.
2. Plants of the new *Osteospermum* are more vigorous than plants of 'Seikilrem'.
3. Plants of the new *Osteospermum* and 'Seikilrem' differ in ray and disc floret color as plants of 'Seikilrem' have lemon yellow-colored ray florets and purple-colored disc florets.

BRIEF DESCRIPTION OF THE PHOTOGRAPHS

The accompanying colored photographs illustrate the overall appearance of the new *Osteospermum* plant showing the colors as true as it is reasonably possible to obtain in colored reproductions of this type. Colors in the photographs may differ slightly from the color values cited in the detailed botanical description which accurately describe the actual colors of the new *Osteospermum* plant.

The photograph at the bottom of the sheet comprises a side perspective view of a typical plant of 'Inostyelow' grown in a container.

The photograph at the top of the sheet is a close-up view of a typical flowering plant of 'Inostyelow'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Osteospermum* production. During the production of the plants, day and night temperatures ranged from 18° C. to 30° C. and light levels averaged 1,500 foot-candles. Plants were seven weeks old when the photographs and description were taken. In the following description, color references are made to The Royal Horticultural Society Colour Chart, 2007 Edition, except where general terms of ordinary dictionary significance are used.

Botanical classification: *Osteospermum hybrida* 'Inostyelow'.

Parentage:

*Female parent*.—*Osteospermum hybrida* 'Balvoyelo', disclosed in U.S. Plant Pat. No. 22,122.

*Male parent*.—Proprietary selection of *Osteospermum hybrida* identified as code number O 09 17-1, not patented.

Propagation:

*Type*.—Terminal cuttings.

*Time to initiate roots, summer*.—About seven days at temperatures ranging from 24° C. to about 27° C.

*Time to initiate roots, winter*.—About eight to ten days at temperatures ranging from 21° C. to about 24° C.

*Time to produce a rooted young plant, summer*.—About four weeks at temperatures ranging from 21° C. to about 24° C.

*Time to produce a rooted young plant, winter*.—About five weeks at temperatures ranging from 17° C. to about 21° C.

*Root description*.—Medium in thickness, fibrous; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Upright and mounding plant habit; inflorescences positioned above and beyond the foliar plane on strong peduncles; moderately vigorous growth habit; moderate growth rate.

*Plant height, soil level to top of foliar plane*.—About 12 cm.

*Plant height, soil level to top of floral plane*.—About 18 cm.

*Plant diameter*.—About 19 cm.

*Lateral branches*.—Quantity per plant: Freely branching habit with about eight primary branches developing per plant, each primary branch with about two to three secondary branches. Length: About 11 cm. Diameter: About 3 mm. Internode length: About 6 mm to 18 mm. Strength: Strong. Aspect: Mostly upright to about 45° from vertical. Texture and luster: Scattered pubescence; matte. Color, developing and fully developed: Close to 146C.

*Leaf description*.—Arrangement: Alternate, simple. Length: About 4.5 cm. Width: About 2.7 cm. Shape: Obovate to spatulate. Apex: Broadly acute. Base: Attenuate. Margin: Mostly entire; often with three to seven points. Texture and luster, upper surface: Scattered pubescence; slightly glossy. Texture and luster, lower surface: Scattered pubescence; matte. Venation pattern: Pinnate, reticulate. Color: Developing leaves, upper surface: Close to 146A. Developing leaves, lower surface: Close to 146B. Fully expanded leaves, upper surface: Close to 147A; venation, close to 146A. Fully expanded leaves, lower surface: Close to 147B; venation, close to 146C. Petioles: Length: About 2.3 cm. Diameter: About 5 mm. Strength: Strong. Texture and luster, upper and lower surfaces: Smooth, glabrous; matte. Color, upper and lower surfaces: Close to 147C.

Inflorescence description:

*Appearance*.—Daisy-type inflorescence form with ligulate-shaped ray florets; inflorescences terminal and axillary and positioned above and beyond the foliar plane on strong peduncles; disc and ray florets developing acropetally on a capitulum; inflorescences face upright to outwardly.

*Flowering habit*.—Freely flowering habit with about 24 inflorescences developing per plant.

*Fragrance*.—None detected.

*Flowering response*.—Plants of the new *Osteospermum* flower early and continuously from spring until frost; long flowering period.

*Inflorescence longevity*.—Inflorescences of plants of the new *Osteospermum* last about five to seven days on the plant; inflorescences persistent.

*Inflorescence buds*.—Height: About 1.8 cm. Diameter: About 1.3 cm. Shape: Broadly ovate. Texture and luster: Smooth, glabrous; matte. Color: Close to 1A.

*Inflorescence size*.—Diameter: Large, about 5.6 cm. Depth (height): About 2.7 cm. Disc diameter: About 1.6 cm. Receptacle diameter: About 2.5 mm. Receptacle height: About 1 cm.

*Ray florets*.—Quantity per inflorescence and arrangement: About 21 arranged in a single whorl. Length: About 3 cm. Width: About 7 mm. Shape: Ligulate. Apex: Shallow emarginate. Base: Attenuate. Margin: Entire. Texture and luster, upper surface: Smooth, glabrous; velvety; matte. Texture and luster, lower surface: Longitudinally ridged, glabrous; velvety; matte. Color: When opening, upper surface: Close to 12A. When opening, lower surface: Close to 12B to 12C; venation, close to 197A. Fully opened, upper surface: Close to 14A; venation, close to 14A; color does not change with development. Fully opened, lower surface: Close to 12B to 12C; midvein, close to 199A to 199B; lateral venation, close to 194B.

*Disc florets*.—Quantity per inflorescence and arrangement: About 76 spirally arranged in numerous whorls at the center of the receptacle. Length: About 8 mm. Diameter, apex: About 3 mm. Diameter, base: About 1 mm. Shape: Tubular; apex, five-pointed with acute points. Texture and luster, inner and outer surfaces: Smooth, glabrous; slightly glossy. Color, immature, inner and outer surfaces: Close to 145B. Color, mature, inner surface: Close to 3B; venation, close to 3B. Color, mature, outer surface: Close to 3B; venation, close to 157C.

*Phyllaries*.—Quantity per inflorescence and arrangement: About 18 to 20 arranged in a single whorl. Length: About 1 cm. Width: About 1 mm. Shape: Lanceolate. Apex: Acuminate. Base: Truncate. Margin: Entire. Texture and luster, upper surface: Smooth, glabrous; glossy. Texture and luster, lower surface: Pubescent, minute; matte. Color, upper surface: Close to 147B. Color, lower surface: Close to 146A.

*Peduncles*.—Length: About 8.8 cm. Diameter: About 1.5 mm. Strength: Strong. Aspect: Mostly upright then leaning outwardly. Texture and luster: Pubescent; minute; matte. Color: Close to 146B.

*Reproductive organs*.—Androecium: Present on disc florets only. Quantity per floret: About five. Filament length: About 2 mm. Filament color: Close to NN155A. Anther shape: Lanceolate. Anther size: About 2 mm by less than 1 mm. Anther color: Close to N200A. Pollen amount: Scarce to moderate. Pollen color: Close to 23A. Gynoecium: Present on both ray and disc florets. Pistil length: About 7 mm to 10 mm. Stigma diameter: Less than 1 mm. Stigma shape: Bi-parted. Stigma color: Close to 15A. Style length: About 2 mm. Style color: Close to NN155A. Ovary color: Close to 157A.

*Seeds and fruits*.—Seed and fruit development has not been observed on plants of the new *Osteospermum*.

Disease & pest resistance: Plants of the new *Osteospermum* have not been shown to be resistant to pathogens and pests common to *Osteospermum* plants.

Garden performance: Plants of the new *Osteospermum* have been observed to have good garden performance and to tolerate rain, wind and to be suitable for USDA Hardiness Zones 9 to 11.

It is claimed:

1. A new and distinct *Osteospermum* plant named 'Inostyelow' as illustrated and described.

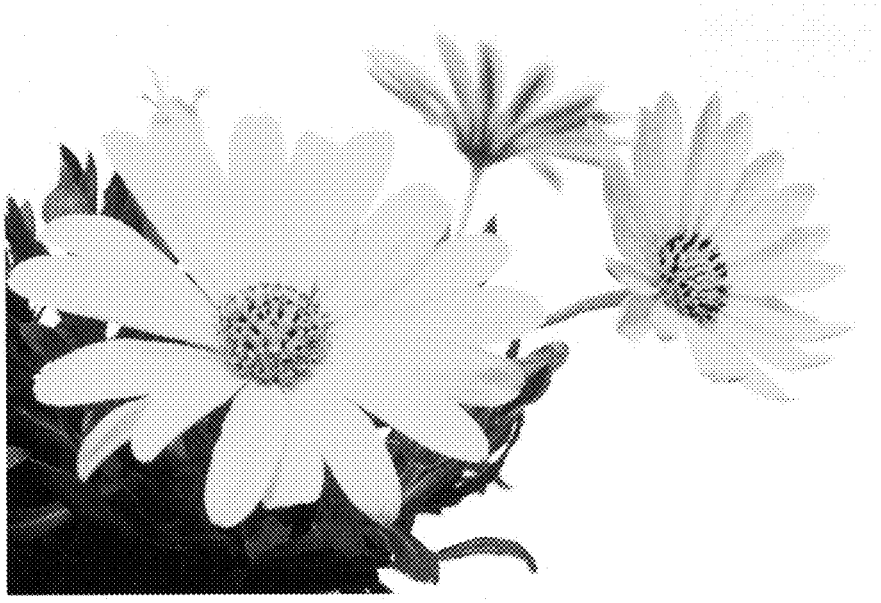
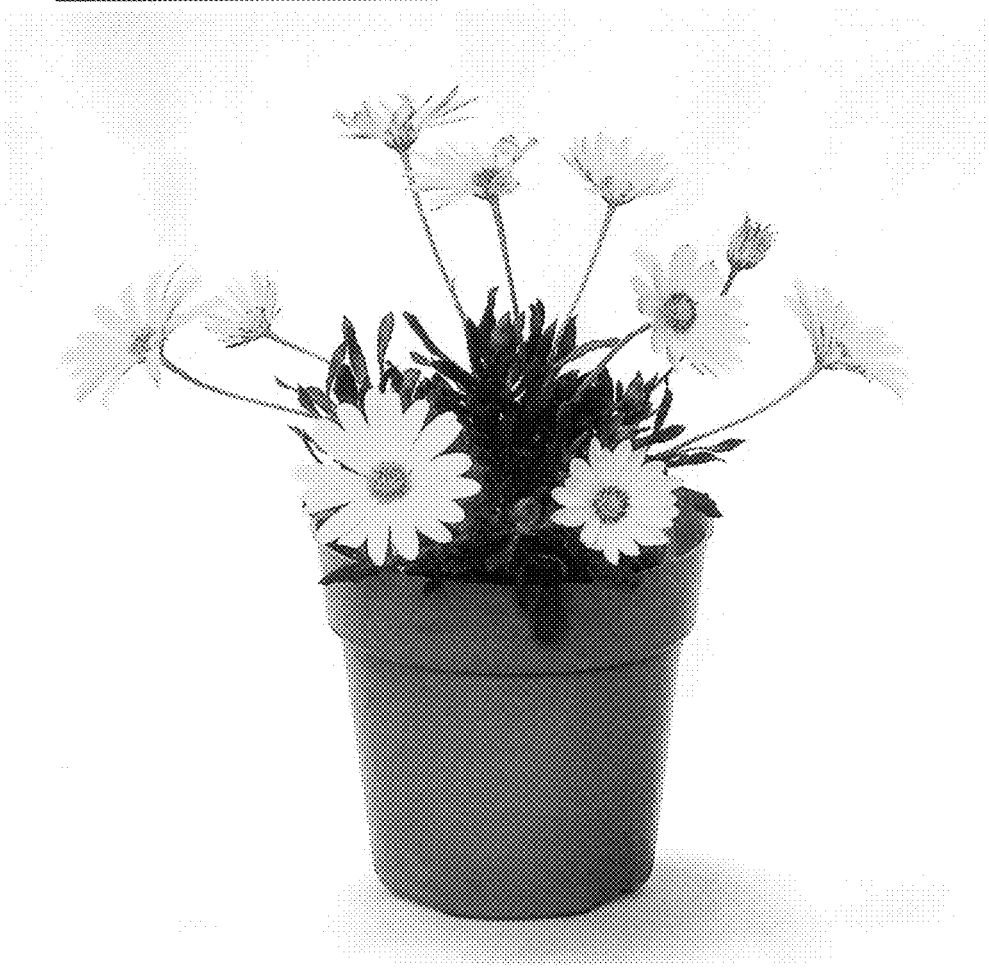

* * * * *